(12) United States Patent
Tseng et al.

(10) Patent No.: US 11,839,452 B2
(45) Date of Patent: Dec. 12, 2023

(54) NON-CONTACT BLOOD PRESSURE MEASUREMENT SYSTEM AND NON-CONTACT BLOOD PRESSURE VALUE CALCULATION METHOD THEREOF

(71) Applicant: NATIONAL TAIWAN UNIVERSITY OF SCIENCE AND TECHNOLOGY, Taipei (TW)

(72) Inventors: Chao-Hsiung Tseng, Taipei (TW); Tzu-Jung Tseng, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 314 days.

(21) Appl. No.: 17/325,407

(22) Filed: May 20, 2021

(65) Prior Publication Data
US 2022/0142492 A1 May 12, 2022

(30) Foreign Application Priority Data
Nov. 11, 2020 (TW) .................................. 109139392

(51) Int. Cl.
*A61B 5/021* (2006.01)
*A61B 5/00* (2006.01)

(52) U.S. Cl.
CPC ........ *A61B 5/02125* (2013.01); *A61B 5/0004* (2013.01); *A61B 5/02116* (2013.01); *A61B 5/7228* (2013.01); *A61B 5/7285* (2013.01)

(58) Field of Classification Search
CPC .............. A61B 5/02125; A61B 5/0004; A61B 5/02116; A61B 5/7228; A61B 5/7285; A61B 5/6824
See application file for complete search history.

(56) References Cited

U.S. PATENT DOCUMENTS

| | | | |
|---|---|---|---|
| 2017/0262987 A1 | 9/2017 | Gnanasambandam et al. | |
| 2022/0133159 A1* | 5/2022 | Ansari | A61B 5/02116 600/502 |
| 2022/0192523 A1* | 6/2022 | Leabman | A61B 5/02438 |

\* cited by examiner

*Primary Examiner* — Patrick Fernandes
*Assistant Examiner* — Joseph A Tombers
(74) *Attorney, Agent, or Firm* — Muncy, Geissler, Olds & Lowe

(57) ABSTRACT

A non-contact blood pressure measurement system and a non-contact blood pressure value calculation method thereof are disclosed. The non-contact blood pressure measurement system includes a measurement module, a signal processing module, and a calculation module. The measurement module measures a physiological signal of a subject being tested in a non-contact manner. The signal processing module is used to obtain a forward pressure wave and a backward pressure wave according to the physiological signal of the subject being tested. The calculation module is used to find out a reflected pulse transit time between the forward pressure wave and the backward pressure wave so as to substitute the reflected pulse transit time and a plurality of correction parameters into a blood pressure algorithm formula to calculate an estimated diastolic blood pressure and an estimated systolic blood pressure of the subject being tested.

16 Claims, 6 Drawing Sheets

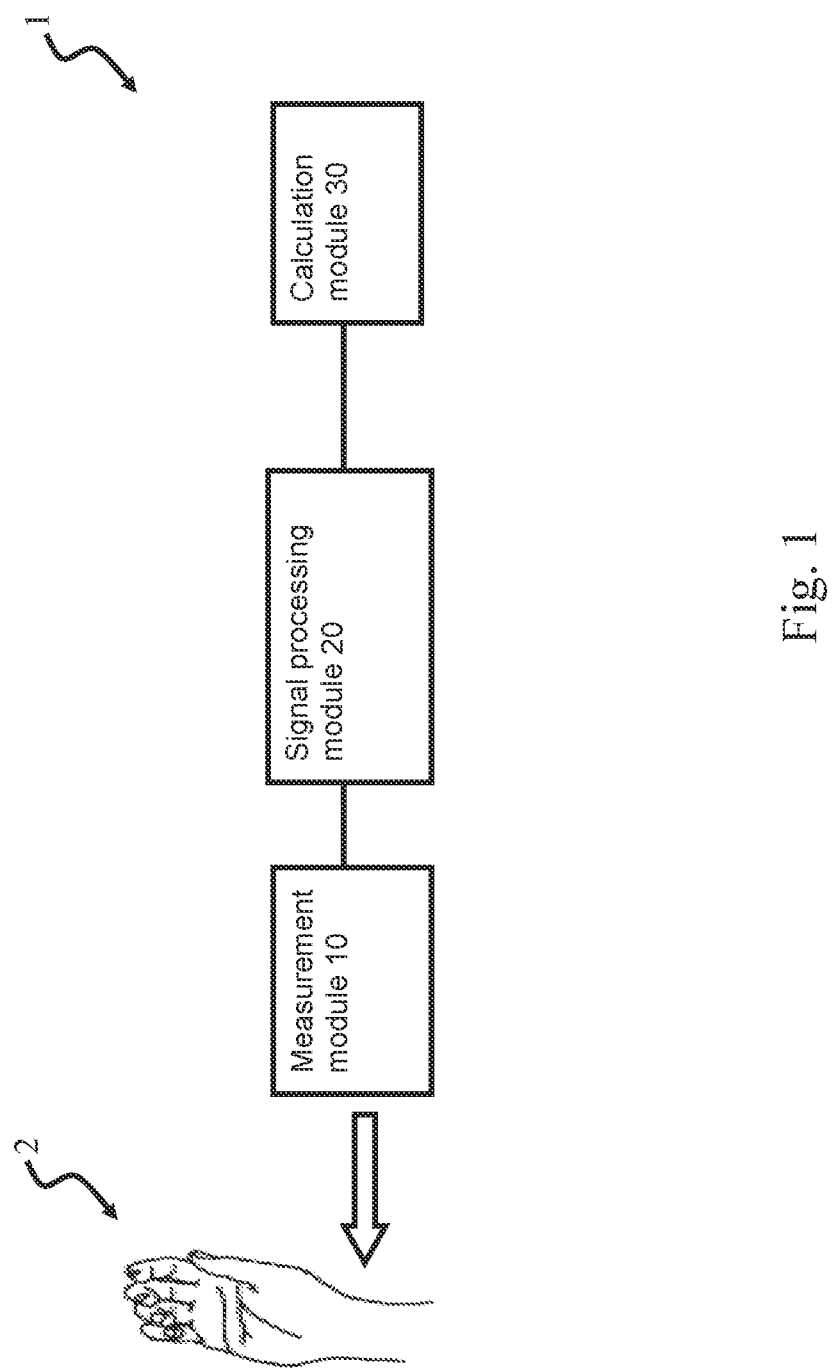

NON-CONTACT BLOOD PRESSURE MEASUREMENT SYSTEM AND NON-CONTACT BLOOD PRESSURE VALUE CALCULATION METHOD THEREOF

BACKGROUND OF THE INVENTION

1. Field of the Invention

The present invention relates to a non-contact blood pressure measurement system and a non-contact blood pressure value calculation method thereof, and more particularly, to a non-contact blood pressure measurement system which uses a pulse transit time difference to calculate a blood pressure and a non-contact blood pressure measurement method thereof.

2. Description of the Related Art

Hypertension is a common disease in modern society. In addition to causing arteriosclerosis, hypertension can also cause heart, brain and kidney related diseases. Therefore, it is very important to measure blood pressure for health maintenance. For subjects being tested, non-invasive blood pressure measurement technology is usually used to measure blood pressure. The non-invasive blood pressure measurement technology can be applied by using a mercury sphygmomanometer or an electronic sphygmomanometer. However, the subject being tested has to wear a compression device to pressurize the arm or other limbs when using a non-invasive sphygmomanometer, and the pressure of the compression device prevents blood circulation and causes discomfort to the subject being tested.

Therefore, in the prior art, there is a non-compressive way to measure the blood pressure of the subject being tested. The prior art technique uses electrocardiography (ECG) of the subject to obtain the heartbeat data of the subject being tested and then uses a photoplethysmography sensor (PPG) to measure the wrist pulse wave signal to obtain the heartbeat data, thereby calculating the pulse transit time (PTT). Then the Moens-Korteweg equation is used to calculate the blood pressure value of the subject being tested. However, this method requires the operation of professional medical equipment, such as using an electrode patch or hand clamping PPG sensor to measure the subject being tested, which could cause discomfort to the subject being tested. Moreover, the above two instruments must be synchronized to obtain the correct pulse transit time, and the synchronization process causes inconvenience to the user.

Therefore, it is necessary to propose a novel non-contact blood pressure measurement system and a non-contact blood pressure value calculation method to solve the deficiencies of the prior art.

SUMMARY OF THE INVENTION

It is a main object of the present invention to provide a non-contact blood pressure measurement system which uses a pulse transit time difference to calculate a blood pressure.

It is another main object of the present invention to provide a non-contact blood pressure measurement method for use in the non-contact blood pressure measurement system mentioned above.

In order to achieve the above objects, the present invention discloses a non-contact blood pressure measurement system for measuring a blood pressure of a subject being tested. The non-contact blood pressure measurement system comprises a measurement module, a signal processing module, and a calculation module. The measurement module measures a physiological signal of a subject being tested in a non-contact manner. The signal processing module is electrically connected with the measurement module to obtain a forward pressure wave and a backward pressure wave according to the physiological signal of the subject being tested. The calculation module is connected with the signal processing module to find out a reflected pulse transit time between the forward pressure wave and the backward pressure wave so as to substitute the reflected pulse transit time and a plurality of correction parameters into a blood pressure algorithm formula to calculate an estimated diastolic blood pressure and an estimated systolic blood pressure of the subject being tested.

The non-contact blood pressure calculation method of the present invention comprises the following steps of: measuring a physiological signal of a subject being tested in a non-contact manner; obtaining a forward pressure wave and a backward pressure wave according to the physiological signal; finding out a reflected pulse transit time between the forward pressure wave and the backward pressure wave; and substituting the reflected pulse transit time and a plurality of correction parameters into a blood pressure algorithm formula to calculate an estimated diastolic blood pressure and an estimated systolic blood pressure of the subject being tested.

BRIEF DESCRIPTION OF THE DRAWINGS

FIG. 1 illustrates a schematic structural view of a non-contact blood pressure measurement system of the present invention;

DETAILED DESCRIPTION OF THE PREFERRED EMBODIMENTS

Figure 2A:
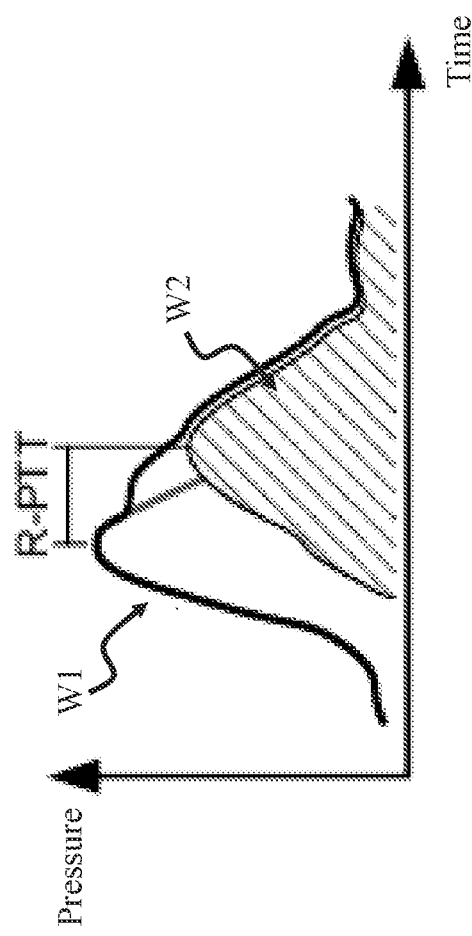
FIG. 2A illustrates a schematic view of different pulses of a subject being tested with the non-contact blood pressure measurement system of the present invention.

In order to make the structure and characteristics as well as the effectiveness of the present invention to be further understood and recognized, the detailed description of the present invention is provided as follows along with embodiments and accompanying figures.

Hereinafter, please refer to FIG. 1 for a schematic structural view of a non-contact blood pressure measurement system of the present invention.

In an embodiment of the present invention, the non-contact blood pressure measurement system 1 can be disposed in a smart wearable device or in an independent medical instrument. The non-contact blood pressure measurement system 1 includes a measurement module 10, a signal processing module 20, and a calculation module 30. The measurement module 10 uses anon-contact method to measure a physiological signal, that is, the pulse of a subject being tested 2 on the finger, wrist or other parts of the body. The measurement module 10 is a self-oscillating complementary split ring resonance element or a radar module. The radar module can be a continuous wave (CW) radar or a frequency-modulated continuous wave (FMCW) radar. Its function will be described in detail later, so it will not be described here. The signal processing module 20 is electrically connected with the measurement module 10 to cooperate with the above-mentioned self-oscillating complementary split ring resonance element or continuous wave radar to obtain a forward pressure wave W1 and a backward pressure wave W2 according to the physiological signal of the subject being tested 2.

Figure 2B:
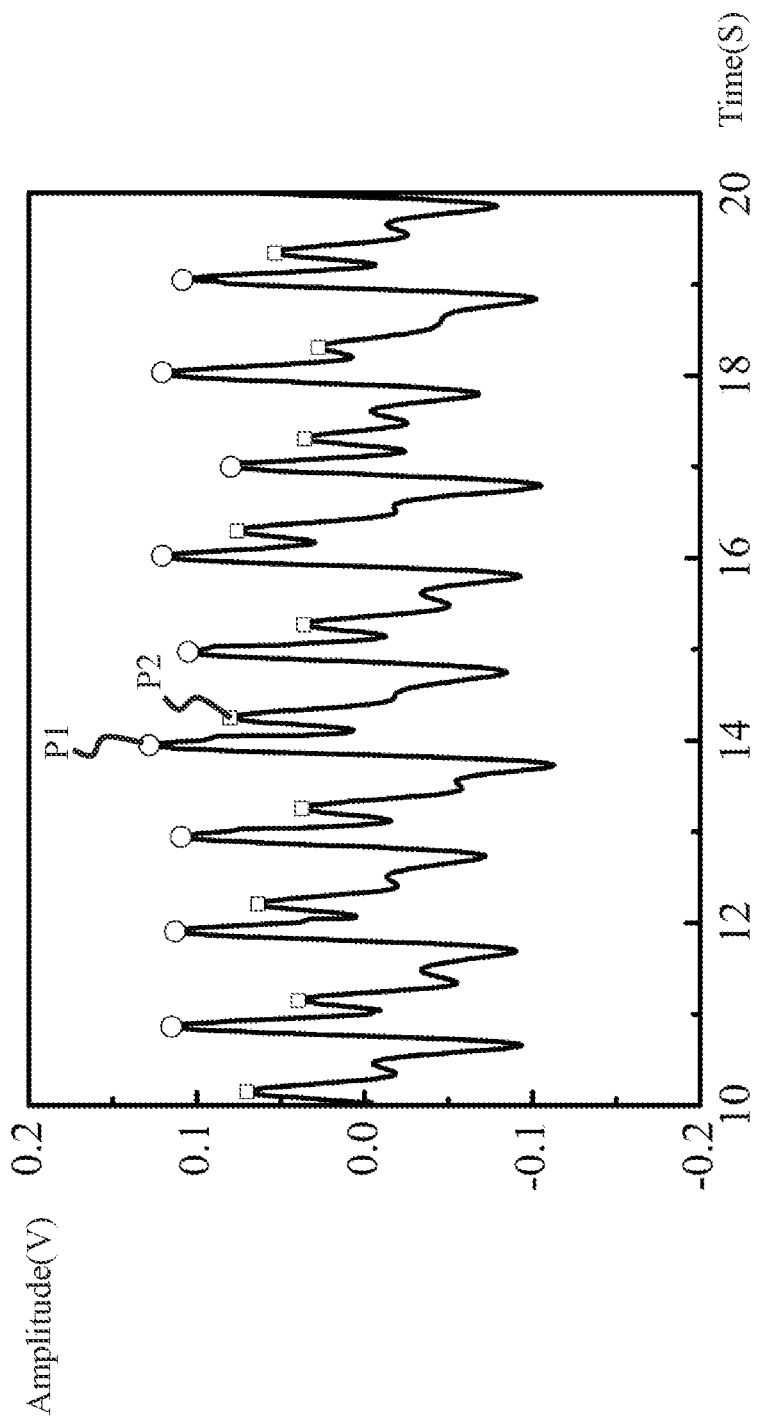
FIG. 2B illustrates a time-domain view of the pulse wave signal of a subject being tested with the non-contact blood pressure measurement system of the present invention.

Please also refer to FIG. 2A for a schematic view of different pulses of a subject being tested with the non-contact blood pressure measurement system of the present invention and FIG. 2B for a time-domain view of the pulse wave signal of a subject being tested with the non-contact blood pressure measurement system of the present invention.

As shown in FIG. 2A, when the pulse wave signal of the blood flowing out of the heart is detected at the measurement point, the main peak that can be observed on the waveform is the maximum amplitude caused by the large amount of blood flowing out when the heart contracts, which is called the forward pressure wave W1; and when the forward pressure wave hits the extremity of the limb, it will cause a reflection signal, which is called the backward pressure wave W2. Since the backward pressure wave W2 is a reflected pressure signal, the signal strength is slightly smaller than that of the forward pressure wave W1. The time difference between the forward pressure wave W1 and the backward pressure wave W2 is a reflected pulse transit time (R-PTT).

The physiological signal measured by the measurement module 10 is also processed by the signal processing module 20. The signal processing module 20 can comprise filters, amplifiers, etc., and the signal processing module 20 is not limited thereto. Since the physiological signal obtained by the measurement module 10 may be subject to noise interference or contain unwanted high-frequency signals, it is not a perfect signal. At this time, the signal processing module 20 can be used to filter out unwanted noise. After the physiological signal is filtered by the signal processing module 20, only the frequency band of the pulse wave signal remains and is outputted to the calculation module 30 for further processing.

The calculation module 30 is electrically connected with the signal processing module 20. The calculation module 30 can be a module in a wearable electronic device or can be disposed in a remote computer system or a smart phone. In the present invention, the measurement module 10 and the signal processing module 20 can be disposed in the same device as the calculation module 30, or the measurement module 10 and the signal processing module 20 can be disposed in a different device. The calculation module 30 can use first-order or second-order differential or slope changes to analyze the pulse wave signal to obtain the waveform shown in FIG. 2B. The calculation module 30 searches for regional peaks to find out the first peak P1 with the highest amplitude and the second peak P2 with the second highest amplitude. The first peak P1 represents the forward pressure wave W1, the second peak P2 represents the backward pressure wave W2, and the time difference between the two peaks is the reflected pulse transit time (R-PTT).

Next, the calculation module 30 substitutes the reflected pulse transit time and a plurality of correction parameters into a blood pressure algorithm formula to calculate and obtain an estimated diastolic blood pressure and an estimated systolic blood pressure of the subject being tested 2. The calculation module 30 can use a measured diastolic blood pressure and a measured systolic blood pressure to first find out the plurality of correction parameters. The measured diastolic blood pressure and the measured systolic blood pressure are the values obtained by a traditional sphygmomanometer. The traditional sphygmomanometer can be a mercury sphygmomanometer or an electronic sphygmomanometer. However, the present invention is not limited thereto.

Regarding to the blood pressure algorithm formula, it can be first derived to find out the pulse wave velocity (PWV) according to the Bramwell-Hill formula:

$$PWV = \sqrt{\frac{V}{\rho}\frac{dP}{dV}} = \frac{L_{rt}}{R\text{-}PTT}$$

wherein V is the blood volume per unit length, ρ is the blood density, dP is the pressure difference between the diastolic and systolic blood pressures, and dV is the change in blood volume. The pulse wave propagation velocity can also be expressed as the round-trip transmission distance (Lrt) divided by the reflected pulse transit time (R-PTT). Then the following formula is obtained:

$$dP = SBP - DBP = \frac{\rho dV}{V}\left(\frac{L_{rt}}{R\text{-}PTT}\right)^2 = \frac{a}{(R\text{-}PTT)^2}$$

wherein a is the first correction parameter. At this time, if the calculation module 30 substitutes the measured diastolic blood pressure into the DBP and the measured systolic blood pressure into the SBP, the value of the first correction parameter can be obtained.

Then the value of PWV can be obtained according to Moens-Korteweg formula:

$$PWV = \sqrt{\frac{E_{in}h}{2\rho r}}$$

wherein Ein is the elastic modulus of the laterally expanded arterial wall, h is the thickness of the arterial wall, and r is the radius of the artery at the end of the diastole. The relationship between Ein and the mean blood pressure (MBP) is:

$$E_{in} = 1428.7 e^{0.031 MBP}$$

Since MBP is defined as ⅓SBP+⅔DBP, the above formula can be further derived as:

$$\frac{1}{3}SBP + \frac{2}{3}DBP = \frac{2}{0.031}\ln\left(\frac{b}{R\text{-}PTT}\right)$$

wherein b is the second correction parameter. At this time, the calculation module 30 substitutes the measured diastolic blood pressure into the DBP and the measured systolic blood pressure into the SBP; thus, the value of the second correction parameter can be obtained.

Based on the above formulae, it can be obtained that:

$$DBP = \frac{2}{0.031}\ln\left(\frac{b}{R\text{-}PTT}\right) - \frac{1}{3}\frac{a}{(R\text{-}PTT)^2}$$

When taking account of the correction parameters, the blood pressure algorithm formula can be finally obtained as:

$$DBP' = DBP_0 + \frac{2}{0.031}\ln\left(\frac{b}{R\text{-}PTT}\right) - \frac{1}{3}\frac{a}{(R\text{-}PTT)^2};$$

$$SBP' = SBP_0 + \frac{2}{0.031}\ln\left(\frac{b}{R\text{-}PTT}\right) + \frac{2}{3}\frac{a}{(R\text{-}PTT)^2};$$

wherein $DBP_0$ is the diastolic blood pressure correction parameter and $SBP_0$ is the systolic blood pressure correction parameter. The calculation module 30 substitutes the measured diastolic blood pressure into DBP' and the measured systolic blood pressure into SBP'; thus, the diastolic blood pressure correction parameter and the systolic blood pressure correction parameter can be calculated.

Therefore, after the reflected pulse transit time (R-PTT) is measured, the calculation module 30 can use the above formula, the first correction parameter, the second correction parameter, the diastolic blood pressure correction parameter, and the systolic blood pressure correction parameter to calculate DBP' and SBP', thereby obtaining the estimated diastolic blood pressure and estimated systolic blood pressure of the subject being tested 2.

Figure 3:
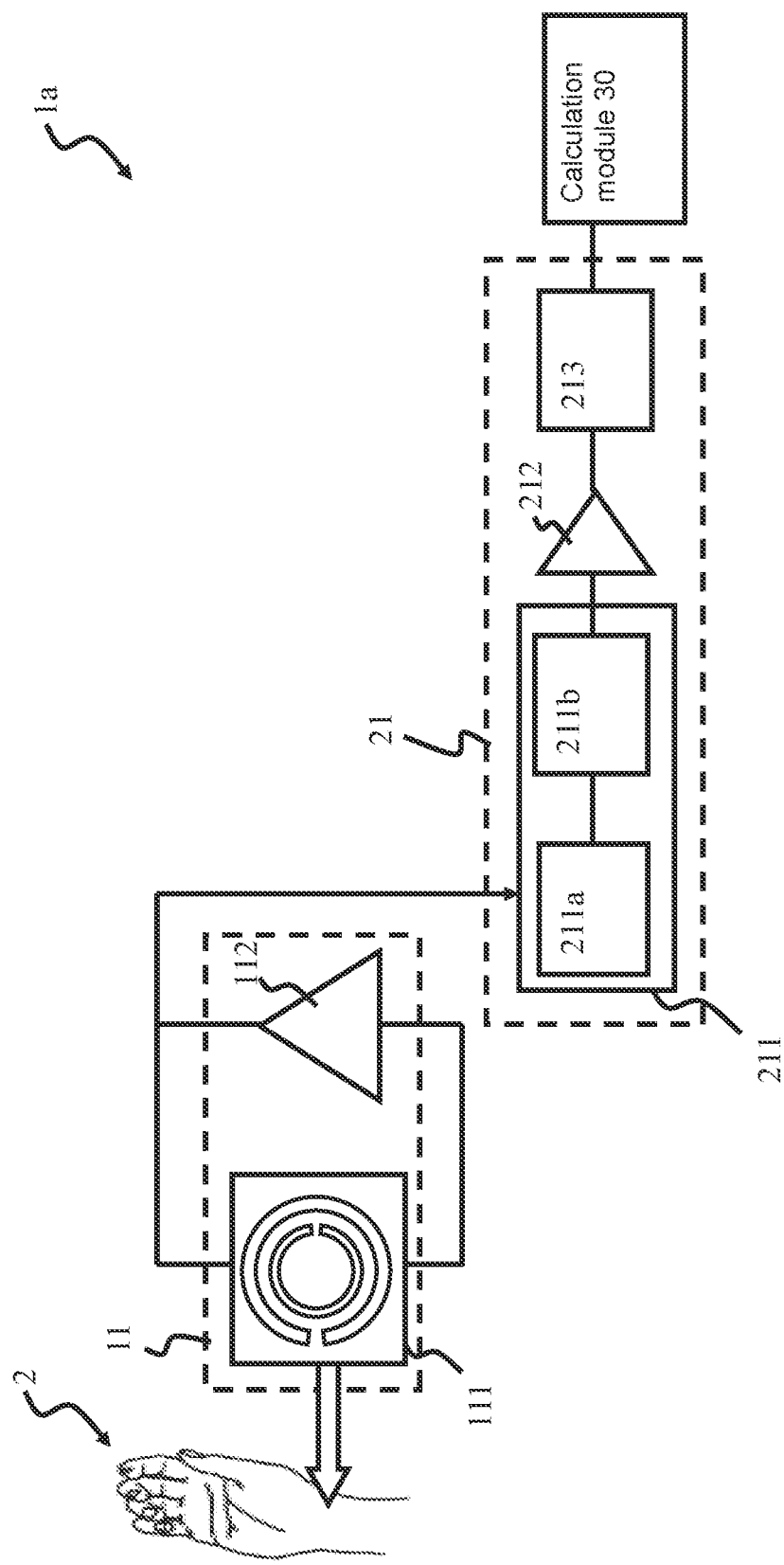
FIG. 3 illustrates a schematic structural view of a first embodiment of the non-contact blood pressure measurement system of the present invention.

For a detailed structure of the non-contact blood pressure measurement system, please refer to FIG. 3, which illustrates a schematic structural view of a first embodiment of the non-contact blood pressure measurement system of the present invention.

In an embodiment of the present invention, a non-contact blood pressure measurement system 1a includes a measurement module 11, a signal processing module 21, and a calculation module 30. The measurement module 11 is a self-oscillating complimentary split ring resonator (SO-CSRR). The SO-CSRR can generate a periodic resonant frequency deviation based on the micro disturbance caused by the blood flow passing through the finger, wrist or other parts of the body of the subject being tested 2, thereby obtaining the physiological signal; therefore, there is no need for the SO-CSRR to be in direct contact with the subject being tested 2. Then, according to the injection-locked theory, the physiological signal is converted into a frequency modulation signal. Therefore, in the first embodiment of the present invention, the measurement module 11 may include a complementary split ring resonator (CSRR) 11l and a bipolar transistor RF amplifier 112. The complementary split ring resonator 111 is implemented in a feedback-loop oscillator configuration. The bipolar transistor RF amplifier 112 is electrically connected with the complementary split ring resonator 111, which can realize a function of sensing oscillation to sense the physiological signal and is used to amplify the frequency modulation signal to provide sufficient gain to meet the Barkhausen oscillation criteria. It should be noted that the use of a bipolar transistor RF amplifier 112 in this embodiment is merely an example, and the present invention is not limited to this type of RF amplifier. Any amplifier that can achieve the same purpose can be used in the present invention.

In a first embodiment of the present invention, the signal processing module 21 can include an amplitude demodulation element 211, an amplifier element 212, and a microcontroller 213. The amplitude demodulation element 211 is electrically connected with the measurement module 11 to receive the output frequency modulation signal of the measurement module 11. The amplitude demodulation element 211 then performs frequency and amplitude modulation. The amplitude demodulation element 211 can be implemented by a microwave differentiator 211a and an envelope detector 211b. Therefore, the microwave differentiator 211a converts the frequency modulation (FM) signal into an amplitude modulation (AM) signal, and the envelope detector 211b converts the radio frequency amplitude into a DC output to obtain the physiological signal of the subject being tested 2. The amplifying element 212 is electrically connected with the amplitude demodulation element 211. The amplifying element 212 then receives and amplifies the above-mentioned physiological signal. The amplifying element 212 then outputs the amplified physiological signal. The microcontroller 213 is electrically connected with the amplifier element 212 to receive the amplified physiological signal, convert the amplified physiological signal into a digital physiological signal, and then transmit the digital physiological signal to the calculation module 30.

Figure 4:
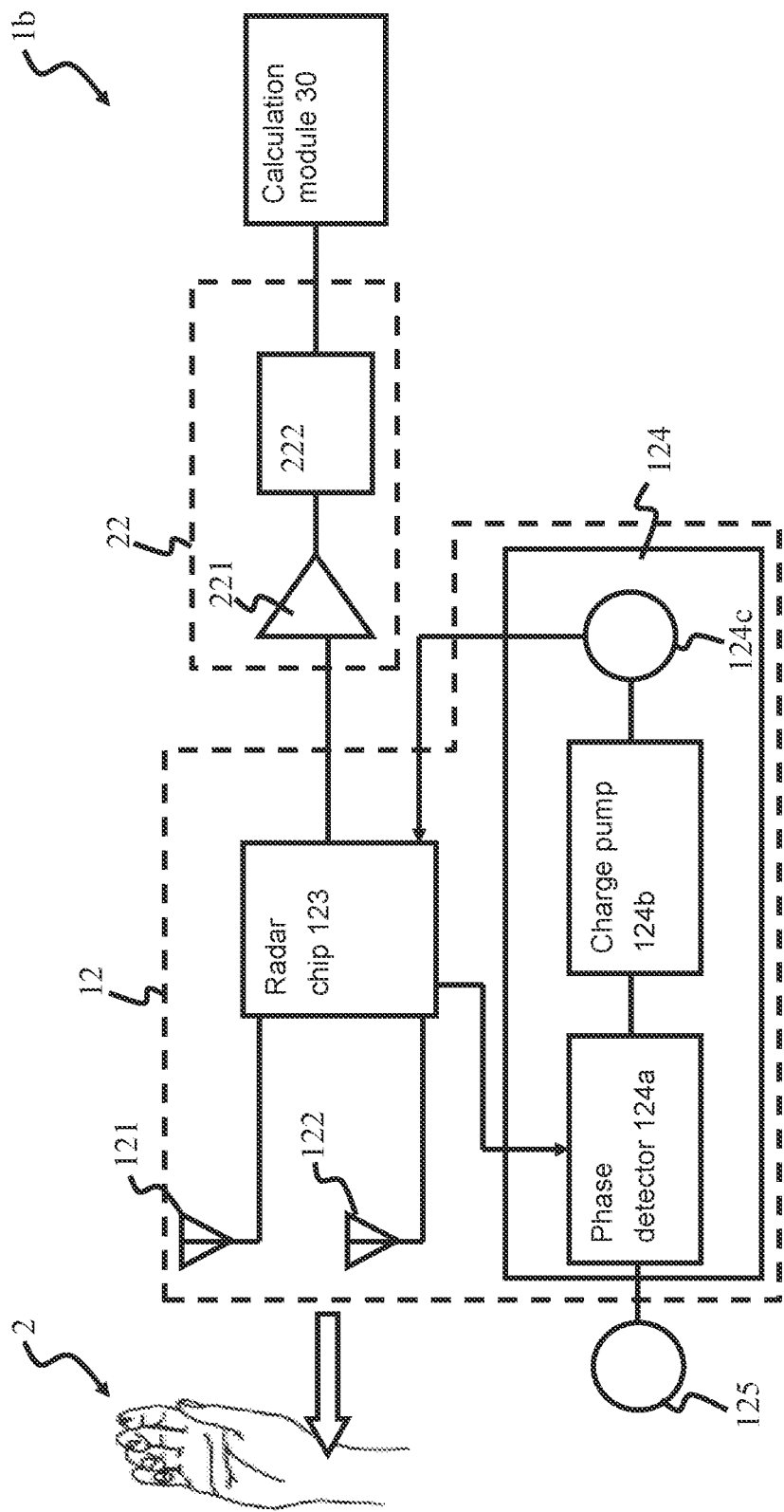
FIG. 4 illustrates a schematic structural view of a second embodiment of the non-contact blood pressure measurement system of the present invention.

Next, please refer to FIG. 4 for a schematic structural view of a second embodiment of the non-contact blood pressure measurement system of the present invention.

In a second embodiment of the present invention, the non-contact blood pressure measurement system 1b includes a measurement module 12, a signal processing module 22, and the calculation module 30. The measurement module 12 is a radar module, e.g., a CW radar or a FMCW radar, which is used to detect the micro disturbance caused by the blood flow passing through the finger, wrist or other parts of the body of the subject being tested 2, without being in direct contact with the subject being tested 2. The measurement module 12 includes two 24 GHz unit antennas 121, 122 of the radar module, a radar chip 123, and a phase-locked loop (PLL) module 124. The unit antennas 121, 122 are used for receiving and transmitting radar waves. The operating frequency of the radar chip 123 is 24 GHz and the operating voltage is 3.3V, and the radar chip 123 has modules such as a low phase noise voltage control oscillator (VCO) and a frequency divider disposed therein to generate 24 GHz radio frequency signals.

The phase locked loop (PLL) module 124 is electrically connected with the radar chip 123 and is used to synchronize the phase of the radio frequency signal source of the radar chip 123 with the phase of a reference signal source. The PLL module 124 mainly includes a phase detector 124a, a charge pump 124b, and a loop filter 124c. The PLL module 124 is used to detect the phase difference between two inputs. The reference signal source of the phase detector 124a can be provided by another oscillator 125. The phase detector 124a compares the phase of the radio frequency signal source with the phase of the reference signal source, uses the charge pump 124b for adjustment according to the phase changes between the two signal sources, and further charges/discharges the loop filter 124c, thereby adjusting the oscillation frequency of the voltage-controlled oscillator in the radar chip 123. This process will repeat until the two input signals of the phase detector 124a are the same, which means they are in the phase locked state. Therefore, the radar chip 123 can output stable 24 GHz radio frequency signals with low noise to obtain physiological signals of better quality.

The signal processing module 22 includes an amplifying element 221 and a microcontroller 222. The amplifying element 221 is electrically connected with the radar chip 123, and the microcontroller 222 is then electrically connected with the amplifying element 221. The amplifying element 221 is used to amplify the physiological signal and then output the amplified physiological signal to the microcontroller 222. The microcontroller 222 receives the amplified physiological signal, converts the amplified physiological signal into a digital physiological signal, and transmits the digital physiological signal to the calculation module 30.

It should be noted that each module of the non-contact blood pressure measurement system 1 can be a hardware device, a software program combined with a hardware device, or a firmware combined with a hardware device. However, the present invention is not limited to the above-mentioned manner. In addition, the embodiment disclosed in the present invention only exemplifies a preferred embodiment of the present invention, and in order to avoid redundant description, not all possible variations and combinations are described in detail. However, those skilled in the art should understand that not all of the above-mentioned modules or elements are necessary. In order to implement the present invention, other detailed conventional modules or elements may also be included. Each module or element may be omitted or modified as required. Other modules or elements may not necessarily exist between two of any modules.

Figure 5:
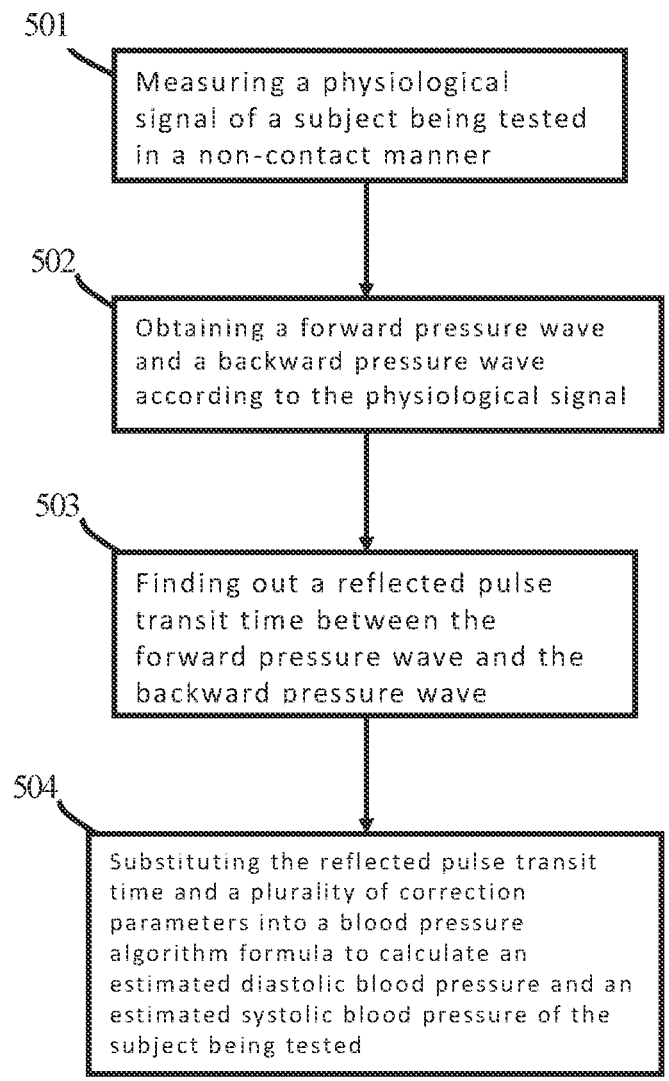
FIG. 5 illustrates a flow chart of the steps of the non-contact blood pressure calculation method of the present invention.

Next, please refer to FIG. 5 for a flow chart of the steps of the non-contact blood pressure calculation method of the present invention. It should be noted that although the non-contact blood pressure measurement system 1 described above is used as an example to illustrate the method for calculating the non-contact blood pressure value of the present invention, the non-contact blood pressure value calculation method of the present invention is not limited to the non-contact blood pressure measurement system having the same structure as the non-contact blood pressure measurement system 1 described above.

First, the method proceeds to step 501: measuring a physiological signal of a subject being tested in a non-contact manner.

The measurement module 10 uses a non-contact method to measure a physiological signal on the finger, wrist or other parts of the body of the subject being tested 2. The measurement module 10 is a self-oscillating complementary split ring resonance element or a radar module.

Then the method proceeds to step 502: obtaining a forward pressure wave and a backward pressure wave according to the physiological signal.

The signal processing module 20 filters the physiological signal of the subject being tested 2 to remove unwanted noise to obtain the forward pressure wave W1 and the backward pressure wave W2.

Then the method proceeds to step 503: finding out a reflected pulse transit time between the forward pressure wave and the backward pressure wave.

The calculation module 30 analyzes the pulse wave signal and looks for regional peaks to find out the first peak P1 with the highest amplitude and the second peak P2 with the second highest amplitude, thereby obtaining a time difference between the forward pressure wave W1 and the backward pressure wave W2. This time difference is a reflected pulse transit time (R-PTT).

Finally the method proceeds to step 504: substituting the reflected pulse transit time and a plurality of correction parameters into a blood pressure algorithm formula to calculate an estimated diastolic blood pressure and an estimated systolic blood pressure of the subject being tested.

The calculation module 30 substitutes the reflected pulse transit time, the first correction parameter, the second correction parameter, the diastolic blood pressure correction parameter, and the systolic blood pressure correction parameter into the blood pressure algorithm formula $$DBP' = DBP_0 + \frac{2}{0.031}\ln\left(\frac{b}{R-PTT}\right) - \frac{1}{3}\frac{a}{(R-PTT)^2}, SBP' =$$
$$SBP_0 + \frac{2}{0.031}\ln\left(\frac{b}{R-PTT}\right) + \frac{2}{3}\frac{a}{(R-PTT)^2}$$

to obtain an estimated diastolic blood pressure and an estimated systolic blood pressure of the subject being tested 2. The calculation module 30 can use a measured diastolic blood pressure and a measured systolic blood pressure to find out the first correction parameter, the second correction parameter, the diastolic blood pressure correction parameter, and the systolic blood pressure correction parameter. The measured diastolic blood pressure and the measured systolic blood pressure are the values obtained by the traditional sphygmomanometer. The traditional sphygmomanometer can be a mercury sphygmomanometer or an electronic sphygmomanometer, or any other suitable type of traditional sphygmomanometer.

Therefore, the calculation module 30 substitutes the measured diastolic blood pressure into DBP and the measured systolic pressure into SBP according to the formula $$dP = SBP - DBP = \frac{a}{(R-PTT)^2},$$

and then the first correction parameter can be obtained. Next, the measured diastolic blood pressure is substituted into DBP and the measured systolic blood pressure into SBP according to the formula $$\frac{1}{3}SBP + \frac{2}{3}DBP = \frac{2}{0.031}\ln\left(\frac{D}{R-PTT}\right),$$

and the second correction parameter can be obtained. Furthermore, substituting the measured diastolic blood pressure into DBP' according to the formula $$DBP' = DBP_0 + \frac{2}{0.031}\ln\left(\frac{b}{R-PTT}\right) - \frac{1}{3}\frac{a}{(R-PTT)^2}$$

yields the diastolic blood pressure correction parameter, and substituting the measured systolic pressure into SBP' according to the formula $$SBP' = SBP_0 + \frac{2}{0.031}\ln\left(\frac{b}{R-PTT}\right) + \frac{2}{3}\frac{a}{(R-PTT)^2}$$

yields the systolic blood pressure correction parameter. Thus, after the reflected pulse transit time R-PTT is measured, the calculation module 30 can use the above formula, the first correction parameter, the second correction parameter, the diastolic blood pressure correction parameter, and the systolic blood pressure correction parameter to find out DBP' and SBP', thereby obtaining the estimated diastolic blood pressure and estimated systolic blood pressure of the subject being tested 2.

It should be noted here that the non-contact blood pressure value calculation method of the present invention is not limited to the above-mentioned sequence of steps, and the above-mentioned sequence of steps can be changed as long as it can achieve the purpose of the present invention.

It can be seen from the above description that the non-contact blood pressure measurement system 1 of the present invention can accurately calculate the blood pressure of the subject being tested 2 without being in direct contact with the subject being tested 2.

As described above, the objective, means, and efficiency of the present invention are all different from conventional characteristics in the prior art. It will be appreciated if the committee can review and grant a patent to benefit the society. However, it should be noted that the embodiments of the present invention described above are only illustrative. All without departing from the scope of the invention are defined solely by the appended claims.

What is claimed is:

1. A non-contact blood pressure value calculation method for use in a non-contact blood pressure measurement system, the method comprising the following steps of:
   using a self-oscillating complimentary split ring resonance element to measure a physiological signal of a subject being tested in a non-contact manner;
   obtaining a forward pressure wave and a backward pressure wave according to the physiological signal;
   finding out a reflected pulse transit time between the forward pressure wave and the backward pressure wave; and
   substitute the reflected pulse transit time and a plurality of correction parameters into a blood pressure algorithm formula to calculate an estimated diastolic blood pressure and an estimated systolic blood pressure of the subject being tested.

2. The non-contact blood pressure value calculation method as claimed in claim 1, the blood pressure algorithm formula comprising:

$$DBP' = DBP_0 + \frac{2}{0.031}\ln\left(\frac{b}{R-PTT}\right) - \frac{1}{3}\frac{a}{(R-PTT)^2};$$

and $$SBP' = SBP_0 + \frac{2}{0.031}\ln\left(\frac{b}{R-PTT}\right) + \frac{2}{3}\frac{a}{(R-PTT)^2};$$

wherein DBP' is the estimated diastolic blood pressure, SBP' is the estimated systolic blood pressure, R-PTT is the reflected pulse transit time, a is a first correction parameter, b is a second correction parameter, $DBP_0$ is a diastolic blood pressure correction parameter, and $SBP_0$ is a systolic blood pressure correction parameter.

3. The non-contact blood pressure value calculation method as claimed in claim 2 further comprising the following steps of:
   substituting a measured diastolic blood pressure and a measured systolic blood pressure into the blood pressure algorithm formula to obtain the plurality of correction parameters.

4. The non-contact blood pressure value calculation method as claimed in claim 3 further comprising the following steps of:
   using a traditional sphygmomanometer to obtain the measured diastolic blood pressure and the measured systolic blood pressure.

5. The non-contact blood pressure value calculation method as claimed in claim 3, wherein
   the first correction parameter is obtained by the formula $$SBP = DBP + \frac{a}{(R-PTT)^2};$$

the second correction parameter is obtained by the formula $$\frac{1}{3}SBP + \frac{2}{3}DBP = \frac{2}{0.031}\ln\left(\frac{b}{R-PTT}\right);$$

wherein DBP is the measured diastolic blood pressure and SBP is the measured systolic blood pressure.

6. The non-contact blood pressure value calculation method as claimed in claim 5, wherein the diastolic blood pressure correction parameter is calculated by substituting the actual measured diastolic blood pressure into the formula $$DBP = DBP_0 + \frac{2}{0.031}\ln\left(\frac{b}{R-PTT}\right) - \frac{1}{3}\frac{a}{(R-PTT)^2};$$

and
the systolic blood pressure correction parameter is calculated by substituting the actual measured systolic pressure into the formula $$SBP = SBP_0 + \frac{2}{0.031}\ln\left(\frac{b}{R-PTT}\right) + \frac{2}{3}\frac{a}{(R-PTT)^2}.$$

7. The non-contact blood pressure value calculation method as claimed in claim 1 further comprising the following steps of:
   using a radar module to measure the physiological signal of the subject being tested.

8. A non-contact blood pressure measurement system for measuring a blood pressure of a subject being tested, the non-contact blood pressure measurement system comprising:
   a measurement module for measuring a physiological signal of a subject being tested in a non-contact manner, wherein the measurement module comprises:
      a self-oscillating complimentary split ring resonance element for measuring the physiological signal of the subject being tested and outputting a frequency modulation signal of the physiological signal; and a bipolar transistor RF amplifier electrically connected with the complementary split ring resonator to realize a sensing oscillation function to output the amplified frequency modulation signal;

a signal processing module electrically connected with the measurement module to obtain a forward pressure wave and a backward pressure wave according to the physiological signal of the subject being tested;

a calculation module electrically connected with the signal processing module to find out a reflected pulse transit time between the forward pressure wave and the backward pressure wave, thereby substituting the reflected pulse transit time and a plurality of correction parameters into a blood pressure algorithm formula to calculate an estimated diastolic blood pressure and an estimated systolic blood pressure of the subject being tested.

9. The non-contact blood pressure measurement system as claimed in claim 8, the blood pressure algorithm formula comprising:

$$DBP' = DBP_0 + \frac{2}{0.031}\ln\left(\frac{b}{R-PTT}\right) - \frac{1}{3}\frac{a}{(R-PTT)^2}; \text{ and}$$

$$SBP' = SBP_0 + \frac{2}{0.031}\ln\left(\frac{b}{R-PTT}\right) + \frac{2}{3}\frac{a}{(R-PTT)^2};$$

wherein DBP' is the estimated diastolic blood pressure, SBP' is the estimated systolic blood pressure, R-PTT is the reflected pulse transit time, a is a first correction parameter, b is a second correction parameter, $DBP_0$ is a diastolic blood pressure correction parameter, and $SBP_0$ is a systolic blood pressure correction parameter.

10. The non-contact blood pressure measurement system as claimed in claim 9, wherein the calculation module substitutes a measured diastolic blood pressure and a measured systolic blood pressure into the blood pressure algorithm formula to obtain the plurality of correction parameters.

11. The non-contact blood pressure measurement system as claimed in claim 10, wherein a traditional sphygmomanometer is used to obtain the measured diastolic blood pressure and the measured systolic blood pressure.

12. The non-contact blood pressure measurement system as claimed in claim 10, wherein
the first correction parameter is obtained by the formula $$SBP = DBP + \frac{a}{(R-PTT)^2};$$

the second correction parameter is obtained by the formula $$\frac{1}{3}SBP + \frac{2}{3}DBP = \frac{2}{0.031}\ln\left(\frac{b}{R-PTT}\right);$$

wherein DBP is the measured diastolic blood pressure and SBP is the measured systolic blood pressure.

13. The non-contact blood pressure measurement system as claimed in claim 12, wherein the diastolic blood pressure correction parameter is calculated by substituting the actual measured diastolic blood pressure into the formula $$DBP = DBP_0 + \frac{2}{0.031}\ln\left(\frac{b}{R-PTT}\right) - \frac{1}{3}\frac{a}{(R-PTT)^2};$$

and
the systolic blood pressure correction parameter is calculated by substituting the actual measured systolic pressure into the formula $$SBP = SBP_0 + \frac{2}{0.031}\ln\left(\frac{b}{R-PTT}\right) + \frac{2}{3}\frac{a}{(R-PTT)^2}.$$

14. The non-contact blood pressure measurement system as claimed in claim 8, wherein the signal processing module comprises:
an amplitude demodulation element electrically connected with the measurement module to perform frequency and amplitude modulation of the physiological signal to obtain an amplitude modulated signal of the physiological signal;
an amplifying element electrically connected with the amplitude demodulation element to receive the amplitude modulated signal and obtain an amplified physiological signal; and a microcontroller electrically connected with the amplifying element to receive the amplified physiological signal and to obtain a digital physiological signal and transmit the digital physiological signal to the calculation module.

15. The non-contact blood pressure measurement system as claimed in claim 8, wherein the measurement module comprises:
a radar module for receiving and transmitting a radar wave;
a radar chip electrically connected with the radar module to obtain a radio frequency signal of the physiological signal; and
a phase-locked loop (PLL) module electrically connected with the radar chip to synchronize the phase of the radio frequency signal of the radar chip with the phase of a reference signal source.

16. The non-contact blood pressure measurement system as claimed in claim 15, wherein the signal processing module comprises:
an amplifying element electrically connected with the radar chip to receive the radio frequency signal and to obtain an amplified physiological signal; and
a microcontroller electrically connected with the amplifying element to receive the amplified physiological signal and to obtain a digital physiological signal and send the digital physiological signal to the calculation module.

* * * * *